United States Patent
Noguchi et al.

(10) Patent No.: US 11,760,816 B2
(45) Date of Patent: Sep. 19, 2023

(54) COMPOUND CONTAINING UNSATURATED DOUBLE BOND, OXYGEN ABSORBER COMPRISING SAME, AND RESIN COMPOSITION

(71) Applicant: KURARAY CO., LTD., Kurashiki (JP)

(72) Inventors: Daiki Noguchi, Tainai (JP); Takashi Fukumoto, Tainai (JP); Katsuji Ujita, Chiyoda-ku (JP); Keiji Kubo, Tsukuba (JP)

(73) Assignee: KURARAY CO., LTD., Kurashiki (JP)

( * ) Notice: Subject to any disclaimer, the term of this patent is extended or adjusted under 35 U.S.C. 154(b) by 504 days.

(21) Appl. No.: 16/764,049

(22) PCT Filed: Nov. 21, 2018

(86) PCT No.: PCT/JP2018/043061
§ 371 (c)(1),
(2) Date: May 14, 2020

(87) PCT Pub. No.: WO2019/107252
PCT Pub. Date: Jun. 6, 2019

(65) Prior Publication Data
US 2021/0024665 A1 Jan. 28, 2021

(30) Foreign Application Priority Data
Nov. 30, 2017 (JP) .................. 2017-231077

(51) Int. Cl.
C08F 16/32 (2006.01)
B01D 53/14 (2006.01)
C08F 20/26 (2006.01)

(52) U.S. Cl.
CPC .............. C08F 16/32 (2013.01); B01D 53/14 (2013.01); C08F 20/26 (2013.01)

(58) Field of Classification Search
None
See application file for complete search history.

(56) References Cited

U.S. PATENT DOCUMENTS

| | | | |
|---|---|---|---|
| 3,644,568 A | 2/1972 | Tilley et al. | |
| 4,481,321 A | 11/1984 | Bruck et al. | |
| 5,045,572 A * | 9/1991 | Plotkin | C07F 7/04 522/170 |
| 5,486,545 A * | 1/1996 | Crivello | C08F 16/32 522/31 |
| 2009/0035696 A1 | 2/2009 | Matsuoka | |
| 2021/0235693 A1 | 8/2021 | Coats et al. | |

FOREIGN PATENT DOCUMENTS

| | | | |
|---|---|---|---|
| CN | 102942460 A | * | 2/2013 |
| CN | 102942460 A | | 2/2013 |
| JP | 57-16001 A | | 1/1982 |
| JP | 59-104338 A | | 6/1984 |
| JP | 59104338 A | * | 6/1984 |
| JP | 63-130610 A | | 6/1988 |
| JP | 5-78459 A | | 3/1993 |
| JP | 61-101518 A | | 5/1996 |
| JP | 9-188645 A | | 7/1997 |
| JP | 09188645 A | * | 7/1997 |
| JP | 2005-99276 A | | 4/2005 |
| JP | 2005099276 A | * | 4/2005 |
| JP | 2013-525564 A | | 6/2013 |
| KR | 10-2012-0018233 | | 3/2012 |
| TW | 200707106 A | | 2/2007 |
| WO | WO 2018/039393 A1 | | 3/2018 |

OTHER PUBLICATIONS

JP 09188645 A, Jul. 1997, Eng. Ab (Year: 1997).*
CN102942460 A, Feb. 2013, Machine Translation (Year: 2013).*
JP 2005099276 A, Apr. 2005, Machine translation (Year: 2005).*
JP 59104338 A, Jun. 1984, Eng. Ab (Year: 1984).*
Extended European Search Report dated Aug. 18, 2021 in European Patent Application No. 18882481.7, 8 pages.
Japanese Office Action dated Jul. 5, 2022 in Japanese Patent Application No. 2019-557188, 3 pages.
Combined Taiwanese Office Action and Search Report dated Mar. 15, 2022 in Taiwanese Patent Application No. 107142389 (with English translation of categories of cited documents), 6 pages.
International Search Report dated Feb. 12, 2019 in PCT/JP2018/043061 filed Nov. 21, 2018, 1 page.
RN 93981-62-5, Database Registry, Entered STN, Aug. 31, 1985, 1 page.
Conceicao, et al., "Supercritical $CO_2$ as an effective medium for a novel conversion of glycerol and alcohols in the heterogeneous telomerisation of butadiene", Green Chemistry, DOI: 10.1039/c2gc16149d, 2012, vol. 14, No. 3, pp. 673-681.
"Air-curable unsaturated polyester resin," Macromolecules, vol. 13, No. 147, 1964, pp. 419-424 (reference previously filed, now submitting partial English language translation), 8 total pages.

* cited by examiner

Primary Examiner — Satya B Sastri
(74) Attorney, Agent, or Firm — Oblon, McClelland, Maier & Neustadt, L.L.P.

(57) ABSTRACT

Provided is an unsaturated double bond-containing compound capable of sufficiently advancing a crosslinking reaction or a curing reaction when used for a coating material or the like and having oxygen absorption performance. The present invention also provides an oxygen absorbent containing the unsaturated double bond-containing compound and a resin composition containing the same. Provided are an unsaturated double bond-containing compound represented by general formula (I), an oxygen absorbent containing the same, and a resin composition.

10 Claims, No Drawings

COMPOUND CONTAINING UNSATURATED DOUBLE BOND, OXYGEN ABSORBER COMPRISING SAME, AND RESIN COMPOSITION

TECHNICAL FIELD

The present invention relates to a specific unsaturated double bond-containing compound, an oxygen absorbent using the same, and a resin composition.

BACKGROUND ART

A radical polymerizable resin such as an unsaturated polyester resin used in a coating material or the like has an unsaturated bond in a polymer main chain and is crosslinked and cured by a vinyl crosslinking agent. When these radical polymerizable resins are used for coating applications, crosslinking is usually carried out in an air atmosphere, and therefore, there are problems in that the crosslinking is easily inhibited by oxygen in the air and the curing is delayed, and in that the surface becomes sticky. As means for preventing these problems, PTL 1 and PTL 2 propose a technique of adding an oxygen absorbent to a resin. In addition, as the oxygen absorbent, allyl glycidyl ether and the like are described in PTL 3 and PTL 4.

CITATION LIST

Patent Literature

PTL 1: JP 63-130610 A
PTL 2: JP 5-78459 A
PTL 3: JP 61-101518 A
PTL 4: U.S. Pat. No. 3,644,568

SUMMARY OF INVENTION

Technical Problem

In coating applications, styrene or the like has been frequently used as a reactive diluent, but from the viewpoint of environmental protection, the trend of conversion into a hardly volatile (meth)acrylic acid ester is increasing. However, when a (meth)acrylic acid ester is used, there is a problem that inhibition by oxygen is more likely to occur than when a conventional reactive diluent is used.

The present invention has been made in view of the above conventional problems, and an object of the present invention is to provide an unsaturated double bond-containing compound having an oxygen absorption performance, which can sufficiently promote a crosslinking reaction or a curing reaction when used in a coating material or the like. Another object of the present invention is to provide an oxygen absorbent containing the unsaturated double bond-containing compound and a resin composition containing the same.

Solution to Problem

As a result of intensive studies, the present inventors have found that an unsaturated double bond-containing compound represented by the following general formula (I) can more stabilize radicals generated than conventional oxygen absorbents and exhibits higher oxygen radical scavenging performance, i.e., oxygen absorption performance, and have made further studies based on this finding to complete the present invention.

That is, the present invention provides [1] to [10] below.

[1] An unsaturated double bond-containing compound represented by the following general formula (I):

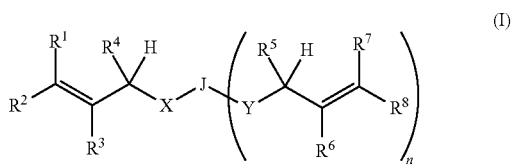

wherein X and Y each independently represent a chalcogen atom; $R^1$, $R^2$, $R^7$, and $R^8$ each independently represent any one of an alkyl group having 1 to 6 carbon atoms, an alkenyl group having 2 to 6 carbon atoms, an aryl group, and an aralkyl group; $R^3$, $R^4$, $R^5$, and $R^6$ each independently represent any one of a hydrogen atom, an alkyl group having 1 to 6 carbon atoms, an alkenyl group having 2 to 6 carbon atoms, an aryl group, and an aralkyl group; J represents a linking group composed of an aliphatic hydrocarbon having 3 to 15 carbon atoms, and the linking group may have any carbon atom substituted with an oxygen atom, and may have at least one substituent selected from the group consisting of a hydroxy group, a (meth)acryloyloxy group, a styryloxy group, and an alkenyloxy group having 2 to 5 carbon atoms; and n is an arbitrary integer of 1 to 5, provided that when a plurality of Y, $R^5$, $R^6$, $R^7$, and $R^8$ are present, they may be different atoms or groups.

[2] The unsaturated double bond-containing compound according to [1], wherein X in the general formula (I) is an oxygen atom.

[3] The unsaturated double bond-containing compound according to [1] or [2], wherein $R^3$ and $R^6$ in the general formula (I) are a hydrogen atom.

[4] The unsaturated double bond-containing compound according to any one of [1] to [3], wherein $R^4$ and $R^5$ in the general formula (I) are each independently a hydrogen atom or a methyl group.

[5] The unsaturated double bond-containing compound according to any one of [1] to [4], which is represented by the following general formula (II):

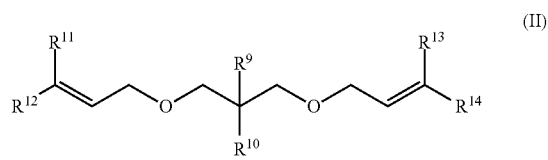

wherein $R^9$ represents a hydrogen atom or a methyl group; $R^{10}$ represents any one of a hydroxy group, a (meth)acryloyloxy group, a styryloxy group, and an alkenyloxy group having 2 to 5 carbon atoms; and $R^{11}$, $R^{12}$, $R^{13}$, and $R^{14}$ each independently represent any one of an alkyl group having 1 to 6 carbon atoms, an alkenyl group having 2 to 6 carbon atoms, an aryl group, and an aralkyl group.

[6] The unsaturated double bond-containing compound according to [5], wherein $R^9$ in the general formula (II) is a hydrogen atom.

[7] An oxygen absorbent containing the unsaturated double bond-containing compound according to any one of [1] to [6].

[8] The oxygen absorbent according to [7], containing 0.001 to 10 mol % of a transition metal salt with respect to the vinyl group in the unsaturated double bond-containing compound.

[9] A resin composition containing the oxygen absorbent according to [7] or [8], and a resin.

[10] The resin composition according to [9], wherein the resin is an active energy ray-curable resin.

Advantageous Effects of Invention

According to the present invention, it is possible to provide an unsaturated double bond-containing compound having an oxygen absorption performance, which can sufficiently promote a crosslinking reaction or a curing reaction when used in a coating material or the like. Further, an oxygen absorbent containing the unsaturated double bond-containing compound and a resin composition containing the same can be provided.

DESCRIPTION OF EMBODIMENTS

<Unsaturated Double Bond-Containing Compound Represented by General Formula (I)>

The unsaturated double bond-containing compound of the present invention is a compound represented by the following general formula (I).

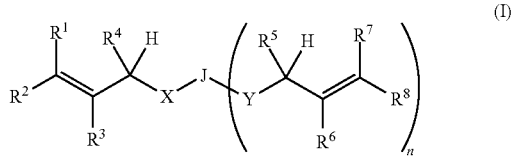

wherein X and Y each independently represent a chalcogen atom; $R^1$, $R^2$, $R^7$, and $R^8$ each independently represent any one of an alkyl group having 1 to 6 carbon atoms, an alkenyl group having 2 to 6 carbon atoms, an aryl group, and an aralkyl group; $R^3$, $R^4$, $R^5$, and $R^6$ each independently represent any one of a hydrogen atom, an alkyl group having 1 to 6 carbon atoms, an alkenyl group having 2 to 6 carbon atoms, an aryl group, and an aralkyl group; J represents a linking group composed of an aliphatic hydrocarbon having 3 to 15 carbon atoms, and the linking group may have any carbon atom substituted with an oxygen atom, and may have at least one substituent selected from the group consisting of a hydroxy group, a (meth)acryloyloxy group, a styryloxy group, and an alkenyloxy group having 2 to 5 carbon atoms; and n is an arbitrary integer of 1 to 5, provided that when a plurality of Y, $R^5$, $R^6$, $R^7$, and $R^8$ are present (i.e., when n is an integer of 2 or more), they may be different atoms or groups.

In the general formula (I), X and Y each independently represent a chalcogen atom. X and Y are each preferably an oxygen atom or a sulfur atom, and more preferably an oxygen atom, from the viewpoint of ease of production of the unsaturated double bond-containing compound and from the viewpoint of improvement in oxygen absorption performance.

In the general formula (I), $R^1$, $R^2$, $R^7$, and $R^8$ each independently represent any one of an alkyl group having 1 to 6 carbon atoms, an alkenyl group having 2 to 6 carbon atoms, an aryl group, and an aralkyl group.

Examples of the alkyl group having 1 to 6 carbon atoms include a methyl group, an ethyl group, an n-propyl group, an isopropyl group, an n-butyl group, an isobutyl group, a sec-butyl group, a tert-butyl group, an n-pentyl group, an isopentyl group, a neopentyl group, an n-hexyl group, a cyclopropyl group, a cyclobutyl group, a cyclopentyl group, and a cyclohexyl group.

Examples of the alkenyl group having 2 to 6 carbon atoms include a vinyl group, an allyl group, a propenyl group, an isopropenyl group, a butenyl group, an isobutenyl group, a pentenyl group, a heptenyl group, a hexenyl group, an iso-3-hexenyl group, and a cyclohexenyl group.

Examples of the aryl group include a phenyl group, a tolyl group, a xylyl group, and a naphthyl group.

Examples of the aralkyl group include a benzyl group, a 2-phenylethyl group, a 2-naphthylethyl group, and a diphenylmethyl group.

Among these, $R^1$, $R^2$, $R^7$, and $R^8$ are each independently preferably an alkyl group having 1 to 6 carbon atoms or an alkenyl group having 2 to 6 carbon atoms, more preferably an alkyl group having 1 to 4 carbon atoms, and still more preferably a methyl group.

In the general formula (I), $R^3$, $R^4$, $R^5$, and $R^6$ each independently represent any one of a hydrogen atom, an alkyl group having 1 to 6 carbon atoms, an alkenyl group having 2 to 6 carbon atoms, an aryl group, and an aralkyl group.

Examples of the alkyl group having 1 to 6 carbon atoms include a methyl group, an ethyl group, an n-propyl group, an isopropyl group, an n-butyl group, an isobutyl group, a sec-butyl group, a tert-butyl group, an n-pentyl group, an isopentyl group, a neopentyl group, an n-hexyl group, a cyclopropyl group, a cyclobutyl group, a cyclopentyl group, and a cyclohexyl group.

Examples of the alkenyl group having 2 to 6 carbon atoms include a vinyl group, an allyl group, a propenyl group, an isopropenyl group, a butenyl group, an isobutenyl group, a pentenyl group, a heptenyl group, a hexenyl group, an iso-3-hexenyl group, and a cyclohexenyl group.

Examples of the aryl group include a phenyl group, a tolyl group, a xylyl group, and a naphthyl group.

Examples of the aralkyl group include a benzyl group, a 2-phenylethyl group, a 2-naphthylethyl group, and a diphenylmethyl group.

Among these, $R^3$, $R^4$, $R^5$, and $R^6$ are each independently preferably a hydrogen atom, an alkyl group having 1 to 3 carbon atoms, an alkenyl group having 2 or 3 carbon atoms, or an aryl group, more preferably a hydrogen atom or a methyl group, and still more preferably a hydrogen atom. In particular, from the viewpoint of improving the oxygen absorption performance of the unsaturated double bond-containing compound, $R^3$ and $R^6$ are each preferably a hydrogen atom, and $R^4$ and $R^5$ are each independently preferably a hydrogen atom or a methyl group, and both are more preferably a hydrogen atom.

In the general formula (I), J represents a linking group composed of an aliphatic hydrocarbon having 3 to 15 carbon atoms, and the linking group may have any carbon atom substituted with an oxygen atom, and may have at least one substituent selected from the group consisting of a hydroxy group, a (meth)acryloyloxy group, a styryloxy group, and an alkenyloxy group having 2 to 5 carbon atoms.

The linking group is preferably an aliphatic hydrocarbon group having 3 to 10 carbon atoms, and more preferably an aliphatic hydrocarbon group having 3 to 5 carbon atoms, from the viewpoint of easy handling of the unsaturated double bond-containing compound.

The linking group may have at least one substituent selected from the group consisting of a hydroxy group, a (meth)acryloyloxy group, a styryloxy group, and an alkenyloxy group having 2 to 5 carbon atoms. Examples of the styryloxy group include a 4-styryloxy group. The alkenyloxy group having 2 to 5 carbon atoms may be a vinyloxy group having 2 to 5 carbon atoms.

The substituent of the linking group is preferably a hydroxy group or a (meth)acryloyloxy group from the viewpoint of improving the oxygen absorption performance of the unsaturated double bond-containing compound.

Specific examples of the linking group include a linking group having any structure represented by the following general formula (J-1), and a linking group represented by the following general formula (J-2) is preferable from the viewpoint of availability of a raw material, and a linking group represented by the following general formula (J-3) is more preferable from the viewpoint of improving the oxygen absorption performance of the unsaturated double bond-containing compound. In the general formulas (J-1) to (J-3), "*" represents a bonding point to X or Y.

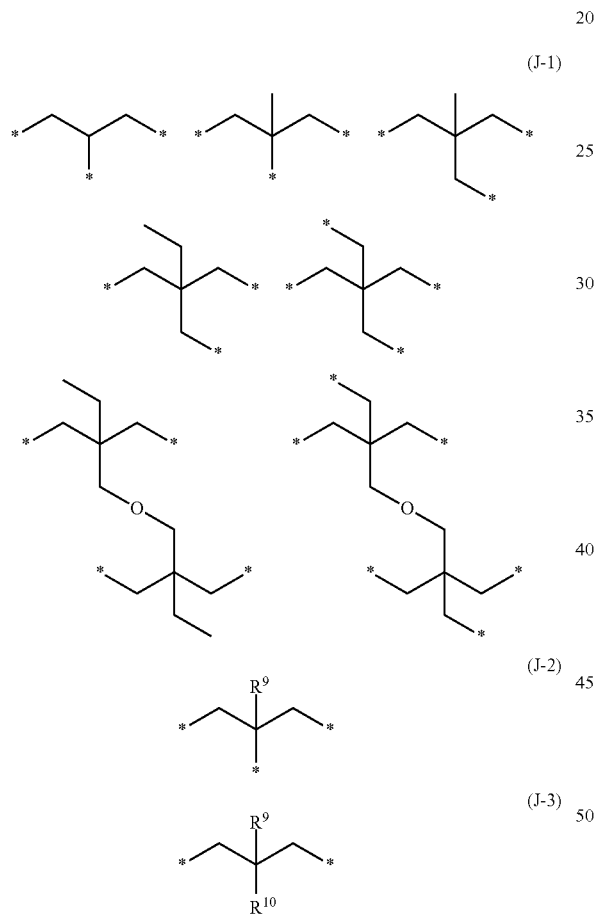

In the general formulas (J-2) and (J-3), $R^9$ represents a hydrogen atom or a methyl group, and is preferably a hydrogen atom. $R^{10}$ represents any one of a hydroxy group, a (meth)acryloyloxy group, a styryloxy group, and an alkenyloxy group having 2 to 5 carbon atoms, and is preferably a hydroxy group or a (meth)acryloyloxy group. The alkenyloxy group having 2 to 5 carbon atoms may be a vinyloxy group having 2 to 5 carbon atoms.

In the general formula (I), n is an arbitrary integer of 1 to 5, preferably 1 to 4, and more preferably 1 or 2 from the viewpoint of availability of a raw material.

Specific examples of the unsaturated double bond-containing compound represented by the general formula (I) include the following compounds, and the unsaturated double bond-containing compound represented by the following general formula (II) is preferable from the viewpoint of the oxygen absorption performance.

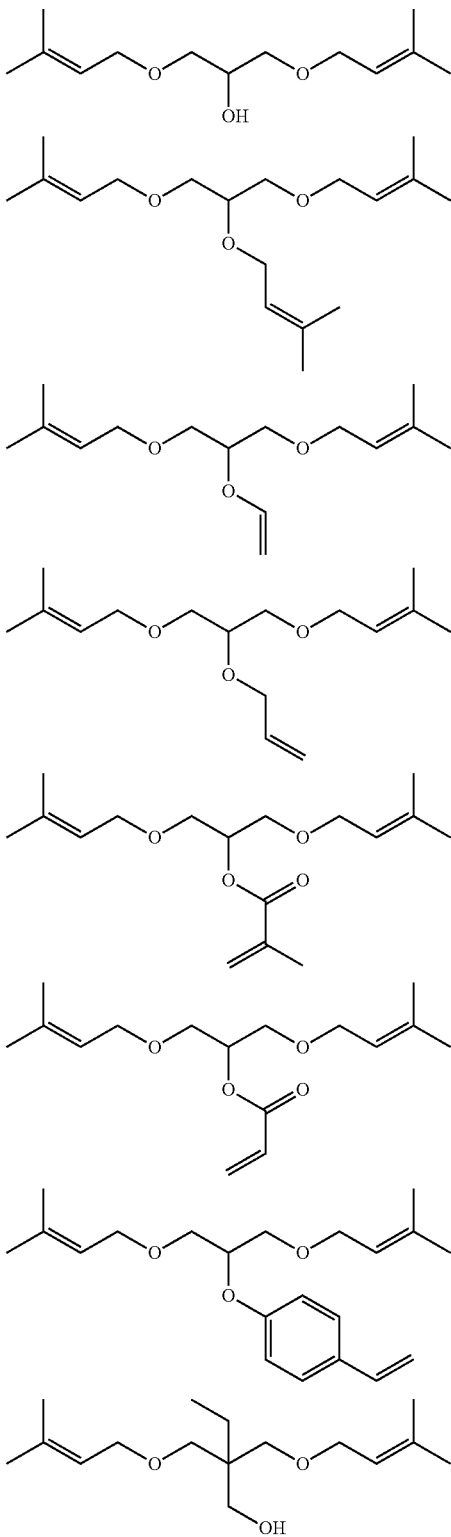

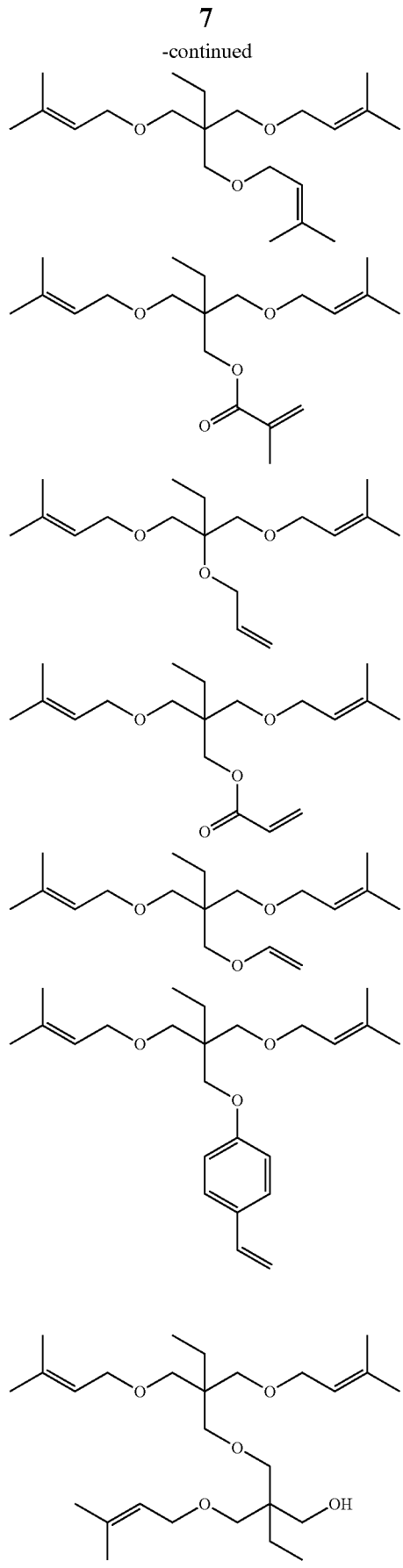

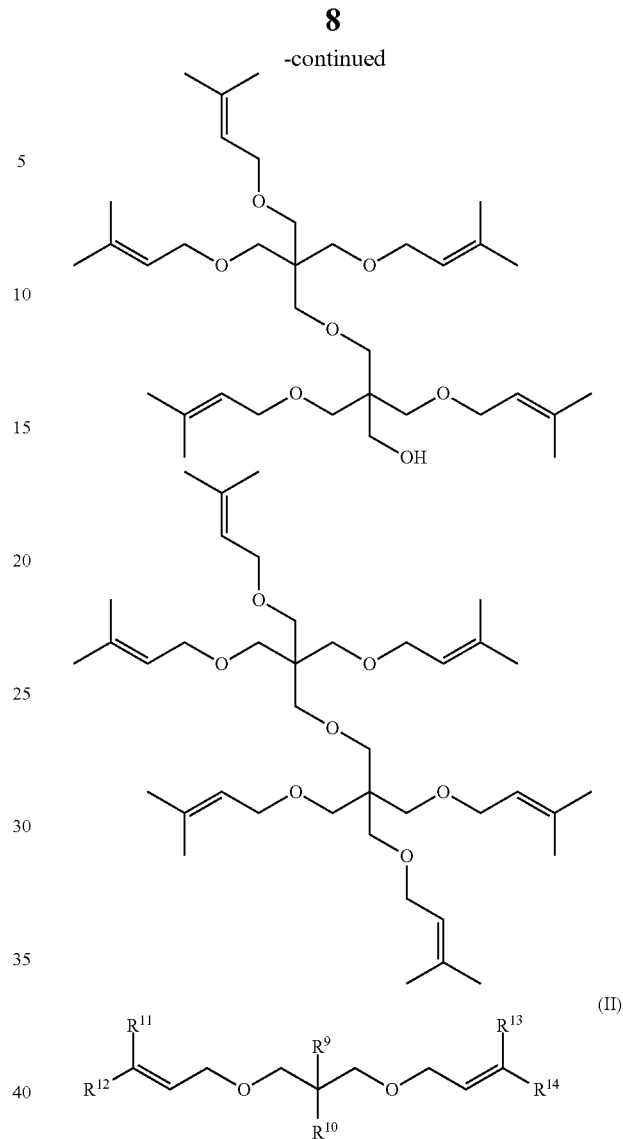

In the general formula (II), $R^9$ represents a hydrogen atom or a methyl group, $R^{10}$ represents any one of a hydroxy group, a (meth)acryloyloxy group, a styryloxy group, and an alkenyloxy group having 2 to 5 carbon atoms, and $R^{11}$, $R^{12}$, $R^{13}$, and $R^{14}$ each independently represent any one of an alkyl group having 1 to 6 carbon atoms, an alkenyl group having 2 to 6 carbon atoms, an aryl group, and an aralkyl group.

In the general formula (II), $R^9$ represents a hydrogen atom or a methyl group, and is preferably a hydrogen atom. $R^{10}$ represents any one of a hydroxy group, a (meth)acryloyloxy group, a styryloxy group, and an alkenyloxy group having 2 to 5 carbon atoms, and is preferably a hydroxy group or a (meth)acryloyloxy group. The alkenyloxy group having 2 to 5 carbon atoms may be a vinyloxy group having 2 to 5 carbon atoms.

In the general formula (II), $R^{11}$, $R^{12}$, $R^{13}$, and $R^{14}$ each independently represent any one of an alkyl group having 1 to 6 carbon atoms, an alkenyl group having 2 to 6 carbon atoms, an aryl group, and an aralkyl group, and preferred embodiments thereof are the same as those of $R^1$, $R^2$, $R^7$, and $R^8$ in the general formula (I).

<Production Method of Unsaturated Double Bond-Containing Compounds>

The method for producing the unsaturated double bond-containing compound of the present invention is not particularly limited, and the compound can be produced by applying known methods alone or in combination. For example, in the case of producing an unsaturated double bond-containing compound represented by the following formula (A-1), the compound can be produced by reacting 3-methyl-2-buten-1-ol, which is a corresponding alcohol, with a compound capable of forming a linking group J, such as epichlorohydrin, in the presence of an alkali, such as potassium hydroxide. As the reaction conditions, from the viewpoint of sufficient reaction, it is preferable to stir at a temperature of about 25 to 70° C. for about 2 to 10 hours.

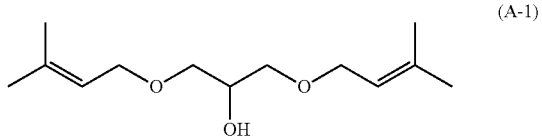 [SMILES: CC(C)=CCOCC(O)COCC=C(C)C]

(A-1)

[Oxygen Absorbent]

The oxygen absorbent of the present invention contains an unsaturated double bond-containing compound represented by the general formula (I). As described above, since the unsaturated double bond-containing compound of the present invention is excellent in the oxygen absorption performance, when an oxygen absorbent containing the unsaturated double bond-containing compound is used in a coating material or the like, a crosslinking reaction or a curing reaction can be sufficiently advanced.

<Transition Metal Salt>

The oxygen absorbent of the present invention has sufficient oxygen absorption performance because it contains the unsaturated double bond-containing compound of the present invention, but may further contain a transition metal salt in order to further improve the oxygen absorption performance.

Examples of the transition metal constituting the transition metal salt include iron, nickel, copper, manganese, cobalt, rhodium, titanium, chromium, vanadium, and ruthenium. Among these, iron, nickel, copper, manganese, and cobalt are preferable, and cobalt is more preferable, from the viewpoint of improving the oxygen absorption performance of the oxygen absorbent.

The counter ion of the transition metal in the transition metal salt is preferably an anion species derived from an organic acid from the viewpoint of compatibility, and examples of the organic acid include acetic acid, stearic acid, dimethyklithiocarbamic acid, palmitic acid, 2-ethylhexanoic acid, neodecanoic acid, linoleic acid, oleic acid, capric acid, and naphthenic acid.

As the transition metal salt to be used in the present invention, any combination of the above transition metal and the above counter ion can be used, but cobalt 2-ethylhexanoate, cobalt neodecanoate, and cobalt stearate are preferable from the viewpoint of the balance between the production cost and the oxygen absorption performance.

When the oxygen absorbent contains a transition metal salt, the content thereof is preferably 0.001 to 10 mol %, more preferably 0.005 to 5 mol %, still more preferably 0.01 to 1 mol %, and even still more preferably 0.1 to 1 mol %, with respect to the vinyl group in the unsaturated double bond-containing compound. The mol % of the content of the transition metal salt is a value with respect to 100 mol of the vinyl group in the unsaturated double bond-containing compound.

When the content of the transition metal salt is within the above range, sufficient oxygen absorption performance can be imparted to the oxygen absorbent.

<Content of Unsaturated Double Bond-Containing Compound in Oxygen Absorbent>

The content of the unsaturated double bond-containing compound represented by the general formula (I) in the oxygen absorbent of the present invention is not particularly limited, but is preferably 50% by mass or more, more preferably 60% by mass or more, still more preferably 70% by mass or more, still more preferably 80% by mass or more, still more preferably 85% by mass or more, and still more preferably 90% by mass or more, from the viewpoint of effectively absorbing oxygen. In addition, from the viewpoint of the production cost of the oxygen absorbent, it is substantially preferably 100% by mass, more preferably 99.9% by mass or less, and still more preferably 99.8% by mass or less.

<Optional Components of Oxygen Absorbent>

The oxygen absorbent of the present invention may contain various additives in addition to the unsaturated double bond-containing compound represented by the general formula (I) and the transition metal salt as long as the effects of the present invention are not impaired. Specifically, the oxygen absorbent may contain a filler, an ultraviolet absorber, a pigment, a viscosity improver, a shrinkage reducing agent, an aging inhibitor, a plasticizer, an aggregate, a flame retardant, a stabilizer, a fiber reinforcement, a dye, an antioxidant, a leveling agent, an anti-sagging agent, and the like.

<Oxygen Absorption Amount>

The oxygen absorbent of the present invention exhibits excellent oxygen absorption performance even at room temperature. Specifically, when the oxygen absorbent of the present invention contains a transition metal salt, the oxygen absorption amount at 20° C. is preferably 2 mL/g or more, more preferably 4 mL/g or more, and still more preferably 6 mL/g or more, as a value after 1 day.

Further, when the oxygen absorbent of the present invention contains a transition metal salt, the oxygen absorption amount at 60° C. is preferably 10 mL/g or more, more preferably 25 mL/g or more, and still more preferably 45 mL/g or more, as a value after 1 day.

On the other hand, when the oxygen absorbent of the present invention does not contain a transition metal salt, the oxygen absorption amount at 20° C. is preferably 1 mL/g or more, more preferably 2 mL/g or more, and still more preferably 2.5 mL/g or more, as a value after 1 day.

Further, when the oxygen absorbent of the present invention does not contain a transition metal salt, the oxygen absorption amount at 60° C. is preferably 10 mL/g or more, more preferably 20 mL/g or more, and still more preferably 25 mL/g or more, as a value after 1 day.

The upper limit of the oxygen absorption amount of the oxygen absorbent is not limited, and the oxygen absorption amount can be measured by the method described in Examples.

<Production Method of Oxygen Absorbent>

The oxygen absorbent of the present invention can be obtained by mixing the unsaturated double bond-containing compound represented by the general formula (I) and, if necessary, a transition metal salt and/or various additives. Specifically, the oxygen absorbent of the present invention can be obtained by stirring and mixing the unsaturated double bond-containing compound represented by the general formula (I) and the transition metal salt.

[Resin Composition]

The resin composition of the present invention contains the oxygen absorbent of the present invention and a resin. Since the unsaturated double bond-containing compound represented by the general formula (I) itself has a polymerizable group or a reactive group, the compound hardly inhibits the crosslinking reaction or polymerization reaction of the resin even when added to the resin. Therefore, the resin composition of the present invention is excellent in that the yield of the crosslinking reaction, the polymerization reaction, or the like of the resin is hardly lowered even in the presence of oxygen.

<Resin>

The resin used in the resin composition of the present invention is not particularly limited as long as it is a resin used in a coating material, an adhesive, a coating agent and the like. The resin may be a radical polymerizable resin or an active energy ray-curable resin such as a UV-curable resin. The resin is preferably an active energy ray-curable resin because the effect of the present invention is more remarkably exhibited depending on the application.

Specific examples of the resin include resins curable by a radical polymerization reaction, such as unsaturated polyester resins, vinyl ester resins, (meth)acrylic resins having a polymerizable group, and urethane (meth)acrylate resins; and resins requiring oxygen barrier properties, such as polyvinyl alcohol, ethylene-vinyl acetate copolymers, partially or completely saponified ethylene-vinyl acetate copolymers, epoxy resins, polyester resins, polyolefin resins, and cyclic polyolefin resins.

In addition to the above resins, a fluororesin, a polyamide resin such as polyamide 66, a polycarbonate resin, a polyurethane resin, or the like may be used as necessary.

Examples of the unsaturated polyester resin include propylene glycol-phthalic anhydride-maleic anhydride copolymer, ethylene glycol-phthalic anhydride-maleic anhydride copolymer, copolymers of a polyhydric alcohol compound with an α,β-unsaturated polybasic acid compound and another polybasic acid compound, and copolymers obtained by adding a radical polymerizable monomer such as styrene to the copolymers.

Examples of the polyhydric alcohol compound include ethylene glycol, 1,2-propanediol, 1,3-propanediol, neopentyl glycol, hydrogenated bisphenol A, and hydrogenated bisphenol F.

Examples of the α,β-unsaturated polybasic acid compound include maleic anhydride, maleic acid, fumaric acid, itaconic acid, and citraconic acid, and examples of the other polybasic acid compound include phthalic anhydride, phthalic acid, isophthalic acid, terephthalic acid, tetrahydrophthalic anhydride, chlorendic acid, adipic acid, and sebacic acid. These may be used alone or in combination of two or more.

These copolymers may further contain a glycidyl compound of an unsaturated alcohol such as allyl glycidyl ether as one of copolymerization components.

Examples of the vinyl ester resin include those obtained by adding (meth)acrylic acid to an epoxy resin, such as those obtained by adding (meth)acrylic acid to the terminal of a bisphenol A type epoxy resin.

Examples of the urethane (meth)acrylate resin include a resin obtained by adding (meth)acrylic acid to an isocyanate group-remaining polymer synthesized from a polyhydric alcohol compound and an excess of a polyhydric isocyanate compound. The polyhydric alcohol compound may be the same as the polyhydric alcohol compound in the description of the unsaturated polyester resin, and examples of the polyhydric isocyanate compound include tolylene diisocyanate, diphenylmethane diisocyanate, isophorone diisocyanate, and hexamethylene diisocyanate.

The content of the unsaturated double bond-containing compound represented by the general formula (I) in the resin composition of the present invention is preferably 0.1 to 50 parts by mass, more preferably 0.2 to 30 parts by mass, and still more preferably 0.5 to 10 parts by mass, with respect to 100 parts by mass of the resin.

<Optional Components of Resin Composition>

The resin composition of the present invention may appropriately contain a pigment, a dye, a filler, an ultraviolet absorber, a viscosity improver, a shrinkage reducing agent, an aging inhibitor, a plasticizer, an aggregate, a flame retardant, a stabilizer, a fiber reinforcement, an antioxidant, a leveling agent, an anti-sagging agent, and the like. In addition, the resin composition of the present invention may contain, for example, styrene, a (meth)acrylic acid ester or the like as a diluent, and it is particularly preferable to contain a (meth)acrylic acid ester from the viewpoint of polymerizable property because the effect of the present invention is more remarkably exhibited.

Examples of the pigment include titanium oxide, red iron oxide, aniline black, carbon black, cyanine blue, and chrome yellow. Examples of the filler include talc, mica, kaolin, calcium carbonate, and clay.

<Production Method of Resin Composition>

The resin composition of the present invention can be obtained by mixing a resin and the oxygen absorbent of the present invention. Specifically, the resin composition of the present invention can be obtained by mixing the oxygen absorbent of the present invention, the resin, and optional components as necessary by stirring or the like.

<Use of Resin Composition>

The resin composition of the present invention can be preferably used for applications such as coating materials, adhesives, and coating agents.

EXAMPLES

Hereinafter, the present invention will be described in detail with reference to examples, but the present invention is not limited to these examples. Measurement of physical properties in Examples and Comparative Examples was carried out by the following methods.

[Method of Measuring Oxygen Absorption Amount (20° C.)]

100 mg of the oxygen absorbent obtained in Examples or Comparative Examples was accurately weighed and put into a sample bottle having a capacity of 20 mL. Thereafter, in order to adjust the humidity in the sample bottle, a vial containing 0.5 mL of ion-exchanged water was put into the sample bottle, and the opening of the sample bottle was closed with a rubber cap sealed with a polytetrafluoroethylene resin and an aluminum seal.

The sample bottle was allowed to stand in a constant temperature bath at 20° C., and after 1 day, 5 days, and 15 days, the residual oxygen amount in the sample bottle was measured using a residual oxygen meter (Pack Master RO-103, manufactured by Iijima Electronics Corporation).

As a control, the residual oxygen amount was measured under the same conditions as in Examples and Comparative Examples, except that the oxygen absorbent obtained in Examples and Comparative Examples was not added, and the difference (oxygen absorption amount) between the measurement values obtained in Examples and Comparative Examples and the measurement value obtained for the control was determined, and the oxygen absorption amount per 1 g of the oxygen absorbent was calculated to be the oxygen absorption amount (20° C.) [mL/g] of the oxygen absorbent. The same test was performed three times, and the average value was adopted.

[Method of Measuring Oxygen Absorption Amount (60° C.)]

In the measurement of the oxygen absorption amount (20° C.), the oxygen absorption amount (60° C.) [mL/g] (the average value of three tests) of the oxygen absorbent was measured in the same manner except that the temperature of the constant temperature bath was changed from 20° C. to 60° C.

Example 1

Synthesis of 1,3-bis(3-methyl-2-butenoxy)-2-hydroxypropane

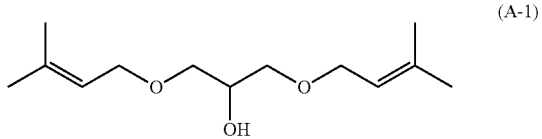 [SMILES: CC(C)=CCOCC(O)COCC=C(C)C]

(A-1)

In a reactor equipped with a stirrer, a thermometer, and a dropping funnel, 61.8 g (0.717 mol) of 3-methyl-2-buten-1-ol and 36.84 g (0.657 mol) of potassium hydroxide were charged under a nitrogen stream. While maintaining the internal temperature at 10° C. or lower, 19.34 g (0.209 mol) of epichlorohydrin was added dropwise with stirring, and the temperature was raised to 50° C. after completion of the dropwise addition. The mixture was stirred at an internal temperature of 50° C. for 6 hours and then cooled to 25° C. The reaction solution was neutralized with a 4M hydrochloric acid aqueous solution, and the upper layer was washed with 310 mL of ion-exchanged water. The obtained organic layer was purified by distillation to obtain 28.77 g (0.126 mol; yield 60.3%) of 1,3-bis(3-methyl-2-butenoxy)-2-hydroxypropane represented by the above general formula (A-1). The results of $^1$H-NMR measurement are shown below.

$^1$H-NMR (400 MHz, CDCl$_3$, TMS) δ: 5.34 (tsept, J=6.8, 1.6 Hz, 2H), 4.00 (d, J=6.8 Hz, 4H), 3.94 (dhex, J=4.4, 1.6 Hz, 1H), 3.49 (dd, J=9.6, 6.4 Hz, 2H), 3.43 (dd, J=9.6, 4.8 Hz, 2H), 2.84 (d, J=4.0 Hz, 1H), 1.74 (s, 6H), 1.67 (s, 6H)

Example 2

Synthesis of 1,3-bis(3-methyl-2-butenoxy)-2-methacryloyloxypropane

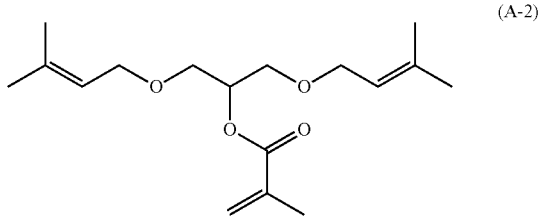 [SMILES: C=C(C)C(=O)OC(COCC=C(C)C)COCC=C(C)C]

(A-2)

In a reactor equipped with a stirrer, a thermometer, and a dropping funnel, 16.1 g of acetonitrile, 11.43 g (0.050 mol) of 1,3-bis(3-methyl-2-butenoxy)-2-hydroxypropane, and 8.41 g (0.083 mol) of triethylamine were charged under an air stream. While maintaining the internal temperature at 15° C. or lower, 6.30 g of methacrylic acid chloride (0.060 mol, containing 2200 ppm of p-methoxyphenol as a polymerization inhibitor) was added dropwise with stirring, and the temperature was raised to 25° C. after completion of the dropwise addition. The mixture was stirred at an internal temperature of 25° C. for 1.5 hours. To the reaction mixture were added 7.07 g of ion-exchanged water and 61 mg of p-dimethylaminopyridine, and the mixture was stirred at 25° C. for 2 hours to confirm decomposition of methacrylic anhydride as a by-product, followed by extraction with ethyl acetate three times. The organic layer was washed with a 2% by mass hydrochloric acid aqueous solution, a 3% by mass sodium hydrogen carbonate aqueous solution, and a saturated saline solution, and dried over sodium sulfate. The obtained organic layer was purified by distillation to obtain 7.70 g (0.026 mol; yield 52%) of 1,3-bis(3-methyl-2-butenoxy)-2-methacryloyloxypropane represented by the above general formula (A-2). The results of $^1$H-NMR measurement are shown below.

$^1$H-NMR (400 MHz, CDCl$_3$, TMS) δ: 6.14 (s, 1H), 5.56 (quin, J=1.6 Hz, 1H), 5.32 (tquin, J=4.0, 1.6 Hz, 2H), 5.18 (quin, J=5.2 Hz, 1H), 3.99 (dq, J=14.8, 3.2 Hz, 4H), 3.62 (d, J=5.2 Hz, 4H), 1.95 (d, J=1.6 Hz, 3H), 1.74 (s, 6H), 1.66 (s, 6H)

Example 3

In a glass sample bottle, 5.00 g (21.9 mmol) of 1,3-bis(3-methyl-2-butenoxy)-2-hydroxypropane produced in Example 1, and 34 mg (0.048 mmol; 0.11 mol % based on vinyl groups in 1,3-bis(3-methyl-2-butenoxy)-2-hydroxypropane) of cobalt (II) stearate (manufactured by FUJIFILM Wako Pure Chemical Corporation; purity: 90% by mass) were added and stirred well to obtain an oxygen absorbent. The evaluation results are shown in Table 1.

Example 4

An oxygen absorbent was obtained in the same manner as in Example 3, except that cobalt (II) stearate was not added. The evaluation results are shown in Table 1.

Comparative Example 1

An oxygen absorbent was obtained in the same manner as in Example 3, except that 5.00 g of a compound (E-1) represented by the following formula (manufactured by Tokyo Chemical Industry Co., Ltd.; purity: 99%; 29.0 mmol) was used instead of 1,3-bis(3-methyl-2-butenoxy)-2-hydroxypropane produced in Example 1, and the amount of cobalt (II) stearate was changed from 34 mg to 44 mg (64 mmol; 0.11 mol % based on the vinyl groups in the compound (E-1)). The evaluation results are shown in Table 1.

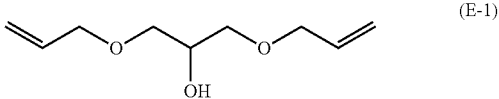

(E-1)

Comparative Example 2

An oxygen absorbent was obtained in the same manner as in Example 4, except that in Example 4, 1,3-bis(3-methyl-2-butenoxy)-2-hydroxypropane was changed to the compound (E-1) (manufactured by Tokyo Chemical Industry Co., Ltd.; purity: 99%) represented by the above formula. The evaluation results are shown in Table 1.

TABLE 1

| | | After 1 day | After 5 days | After 15 days |
|---|---|---|---|---|
| Oxygen absorption amount (20° C.) [mL/g] | Example 3 | 6.9 | 44.6 | 44.9 |
| | Example 4 | 2.6 | 2.6 | 6.4 |
| | Comparative Example 1 | 2.5 | 29.0 | 32.2 |
| | Comparative Example 2 | 0.6 | 0.5 | 1.4 |
| Oxygen absorption amount (60° C.) [mL/g] | Example 3 | >49 | >49 | >49 |
| | Example 4 | 27.6 | >49 | >49 |
| | Comparative Example 1 | 40.0 | >49 | >49 |
| | Comparative Example 2 | 5.8 | 42.5 | >49 |

As shown in Table 1, it is understood that the unsaturated double bond-containing compound of the present invention has excellent oxygen absorption ability even at room temperature. Further, it is surprisingly found that oxygen can be absorbed without using a transition metal salt, and a cross-linking reaction or a curing reaction of the resin composition can be sufficiently developed.

[Effect of Preventing Polymerization Inhibition of UV Curable Resin]

A test for confirming the effect of the UV-curable resin on prevention of polymerization inhibition by oxygen was conducted by the following method.

A PET film (polyethylene terephthalate film; thickness: 125 μm) having a hole with a diameter of 3 cm was stuck on the PET film having no hole to prepare a cell.

Next, 100 parts by mass of 1,9-diacryloylnonane (manufactured by Osaka Organic Chemical Industry Ltd.) and 3 parts by mass of Irgacure 184 (manufactured by BASF) as a photopolymerization initiator were mixed, and 1 part by mass of the unsaturated double bond-containing compound produced in Examples was further added and mixed to obtain a UV-curable composition. This was placed in the cell, and UV curing was performed under the irradiation conditions of an illuminance of 150 W/cm$^2$ and an integrated light amount of 300 mJ/cm$^2$. Then, the surface of the cured product was wiped with acetone-impregnated cotton, the weight change before and after the wiping was measured, and the thickness of the resin portion which was an uncured portion was calculated from the measured value and the specific gravity of the UV-curable composition.

Example 5

As the unsaturated double bond-containing compound of Examples in the above-mentioned polymerization inhibition prevention effect test of the UV-curable resin, 1,3-bis(3-methyl-2-butenoxy)-2-hydroxypropane produced in Example 1 was used. The results are shown in Table 2.

Example 6

A test was carried out in the same manner as in Example 5, except that 1,3-bis(3-methyl-2-butenoxy)-2-hydroxypropane in Example 5 was changed to 1,3-bis(3-methyl-2-butenoxy)-2-methacryloyloxypropane produced in Example 2. The results are shown in Table 2.

Comparative Example 3

The test was carried out in the same manner as in Example 5, except that the unsaturated double bond-containing compound produced in Example 1 was not added. The results are shown in Table 2.

TABLE 2

| | Thickness of Uncured portion (μm) |
|---|---|
| Example 5 | 4.0 |
| Example 6 | 2.3 |
| Comparative Example 3 | 7.1 |

As shown in Table 2, the unsaturated double bond-containing compound of the present invention has a large effect of preventing polymerization inhibition of the active energy ray-curable resin by oxygen, and by adding the unsaturated double bond-containing compound of the present invention, good curability can be imparted to a UV coating material, a UV ink or the like even in the presence of air or in an environment where oxygen may be present.

INDUSTRIAL APPLICABILITY

The oxygen absorbent of the present invention can be suitably used as an oxygen absorbent for suppressing an adverse effect of oxygen in a crosslinking reaction or a curing reaction of a resin including a curing process involving a radical polymerization reaction of an unsaturated polyester resin, a vinyl ester resin, a (meth)acrylic resin, or a urethane (meth)acrylate resin. In addition, by mixing in a resin or coating on the surface, oxygen barrier performance can be improved in a resin such as polyvinyl alcohol, a partially or completely saponified ethylene-vinyl acetate copolymer, or the like in which oxygen barrier properties are required.

The invention claimed is:

1. An unsaturated double bond-containing compound represented by the following general formula (I):

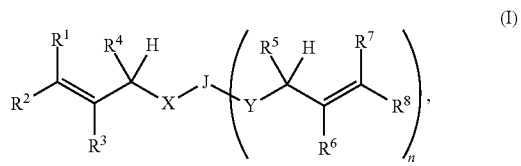

wherein:
X and Y each independently represent a chalcogen atom;
$R^1$, $R^2$, $R^7$, and $R^8$ each independently represent any one selected from the group consisting of an alkyl group having 1 to 6 carbon atoms, an alkenyl group having 2 to 6 carbon atoms, an aryl group, and an aralkyl group;
$R^3$, $R^4$, $R^5$, and $R^6$ each independently represent any one selected from the group consisting of a hydrogen atom, an alkyl group having 1 to 6 carbon atoms, an alkenyl group having 2 to 6 carbon atoms, an aryl group, and an aralkyl group;
J represents a linking group composed of an aliphatic hydrocarbon having 3 to 15 carbon atoms, wherein any carbon atom of the linking group is optionally substituted with an oxygen atom, and wherein the linking group has at least one substituent selected from the group consisting of a (meth)acryloyloxy group, a styryloxy group, and an alkenyloxy group having 2 to 5 carbon atoms;

n is an arbitrary integer of 1 to 5; and when a plurality of Y, $R^5$, $R^6$, $R^7$, and $R^8$ are present, they are each optionally different atoms or groups.

2. The unsaturated double bond-containing compound according to claim 1, wherein X in the general formula (I) is an oxygen atom.

3. The unsaturated double bond-containing compound according to claim 1, wherein $R^3$ and $R^6$ in the general formula (I) are a hydrogen atom.

4. The unsaturated double bond-containing compound according to claim 1, wherein $R^4$ and $R^5$ in the general formula (I) are each independently a hydrogen atom or a methyl group.

5. An unsaturated double bond-containing compound represented by the following general formula (II):

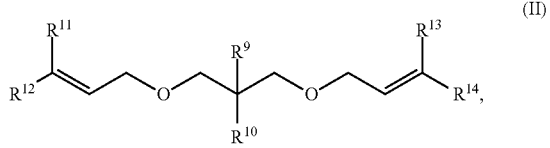

(II)

wherein:

$R^9$ represents a hydrogen atom or a methyl group;

$R^{10}$ represents any one selected from the group consisting of a hydroxy group, a (meth)acryloyloxy group, a styryloxy group, and an alkenyloxy group having 2 to 5 carbon atoms; and $R^{11}$, $R^{12}$, $R^{13}$, and $R^{14}$ each independently represent any one selected from the group consisting of an alkyl group having 1 to 6 carbon atoms, an alkenyl group having 2 to 6 carbon atoms, an aryl group, and an aralkyl group.

6. The unsaturated double bond-containing compound according to claim 5, wherein $R^9$ in the general formula (II) is a hydrogen atom.

7. An oxygen absorbent comprising the unsaturated double bond-containing compound according to claim 5.

8. The oxygen absorbent according to claim 7, comprising 0.001 to 10 mol % of a transition metal salt with respect to the vinyl group in the unsaturated double bond-containing compound.

9. A resin composition, comprising the oxygen absorbent according to claim 7 and a resin.

10. The resin composition according to claim 9, wherein the resin is an active energy ray-curable resin.

\* \* \* \* \*